United States Patent [19]

Zatko et al.

[11] Patent Number: 4,800,000
[45] Date of Patent: Jan. 24, 1989

[54] LOW LEVEL MOISTURE MEASUREMENT SYSTEM AND METHOD

[75] Inventors: David A. Zatko, North Wales, Pa.; John F. Maguire, Riverton, N.J.

[73] Assignee: Manufacturers Engineering Equipment Corp., Warrington, Pa.

[21] Appl. No.: 57,508

[22] Filed: Jun. 3, 1987

[51] Int. Cl.$^4$ ............................................. G01N 27/42
[52] U.S. Cl. .................................... 204/1 T; 204/406; 204/409; 204/430
[58] Field of Search ............. 204/430, 1 W, 406, 409; 338/34

[56] References Cited

U.S. PATENT DOCUMENTS

| | | | |
|---|---|---|---|
| 2,816,067 | 12/1957 | Keidel | 204/130 |
| 2,830,945 | 4/1958 | Keidel | 204/430 |
| 3,240,693 | 3/1966 | Gardner | 204/430 |
| 3,474,006 | 10/1969 | Glassbrook | 204/1 T |

OTHER PUBLICATIONS

F. A. Keidel, Anal. Chem., 31, 2043, (1959).
DuPont Co. Handbook, "Process Instruments", pp. vi, i, 28, 29/30, 34, A-1, A-2 and A-3, 11/83.

Primary Examiner—G. L. Kaplan
Attorney, Agent, or Firm—Ratner & Prestia

[57] ABSTRACT

Water in a gas is measured with improved sensitivity to low levels (on the order of 2.000 to 0.005 ppmv), response time and cell longevity, by an electrolytic cell wherein the electrode element comprises a tubular conduit for the gas having a pair of electrode wires helically positioned in parallel on the interior wall of the conduit from end to end, the wires being coated, except for small portions adjacent the inlet and outlet of the conduit, with a water absorbent crystalline coating comprising a mixture of phosphoric acid or a derivative thereof and an alkylene ($C_2$-$C_4$) oxide polymer selected from a polyalkylene glycol of average molecular weight of at least 500 and an ether or ester thereof having an average molecular weight of at least 300.

19 Claims, 3 Drawing Sheets

LOW LEVEL MOISTURE MEASUREMENT SYSTEM AND METHOD

TECHNICAL FIELD

This invention relates to the electrolytic measurement of moisture in a gas. More particularly, the invention concerns the determination of water at very low levels, on the order of about 2.000 to 0.005 parts per million by volume (ppmv), in a gaseous stream.

BACKGROUND OF THE INVENTION

The measurement of water in gases is critical in chemical process industries because awareness and control of the water content in feed streams, reaction mixtures and product streams often determines the efficiency of a manufacturing process, quality of the product, and overall success of the process. The need to monitor chemical process streams and products either continuously or in batch operations has led to the development of a variety of sophisticated analytical instruments for such purpose. However, many of these instruments are highly complex and expensive, lack portability or longevity, are unable to measure small amounts of water directly and reliably, or exhibit a response time which is too slow for many applications.

Electrolytic measurement of water is extensively reviewed in Smith & Mitchell, Aquametry: Part II, Electrical and Electronic Methods—A Treatise on Methods For The Determination of Water, Second Edition, John Wiley & Sons (1984), 1352 pages, especially Section III: Coulometric Hygrometry, pages 51514 -991. A well-known electrolytic cell described in the Smith & Mitchell text, in U.S. Pat. Nos. 2,816,067 and 2,830,945 to F. A. Keidel and in F. A. Keidel, "Determination of Water by Direct Amperometric Measurement", Analytical Chemistry 31, 2043–2048 (1959) utilizes electrode wiring in a tubular conduit with a phosphoric acid-derived coating over the wires to absorb water in a gas passed through the conduit. The absorbed water is electrolyzed by application of a suitable potential across the wires. Since electrical current consumption in the electrolysis of the water removed from the gas is governed by Faraday's Law, the quantity of water in the gas is directly measurable. (The foregoing publications and patents are incorporated herein by reference).

Although the Keidel cell is portable, the versions of the cell developed to date exhibit slow response times when the cell is dried down to a baseline dry state between determinations, requiring on the order of 1 to 5 hours to measure reduction of water in a dry inert gas stream from 5 to 1 ppmv or less. The "dry down" response time reflects and is a measure of the response time during continuous operation of the cell. In addition, continuous monitoring of modern process streams and reduction of downtime for correction of composition and flow rate of the streams requires cells having superior longevity and durability. While a longevity of several days may be adequate in some systems, capability of operation for weeks and even months can be a significant contributor to the efficiency and economy of a manufacturing sequence and quality of the product. Accordingly, the dominant criteria for an improved water measurement system are sensitivity to low water content, of the order of about 2.0 to 0.005 ppmv, fast response time for measurement of the low water levels, and extended system longevity, of the order of several weeks to months. Other important criteria include portability of the measuring apparatus and capability of making water determinations directly, i.e., without need for comparison with a standard.

SUMMARY OF THE INVENTION

According to one aspect of the invention, the aforementioned advantages are achieved in an electrolytic cell of the Keidel type by placement of the electrolyzing wires so as to cover substantially the entire face of the wall of the conduit exposed to the gas whose water content is to be determined, and in another aspect by coating the wires with a water-absorbent film which contains, in addition to a phosphoric acid-derived crystalline material, a water soluble alkylene oxide polymer. It is believed that the polymer reinforces the phosphoric acid-derived crystalline film to prevent discontinuity therein, which discontinuity results in disruption of the electrolysis or incomplete electrolysis.

In a further aspect of the invention, portions of the wires adjacent the gas inlet and gas outlet of the tubular conduit of the cell are free of the phosphoric acid-derived absorbent coating. This feature and the placement of the wire windings within the tubular conduit eliminate or reduce the possibility of regions in the cell where moisture can collect without being electrolyzed, which reservoirs of moisture necessarily result in lack of sensitivity of the cell and even false readings.

In still another aspect of the invention, the absorbent coating-free portions of the wires are achieved by the technique of (1) coating substantially the entire surface of the wires in the conduit with an aqueous solution of phosphoric acid and a water soluble alkylene oxide polymer, (2) passing a dry inert gas through the conduit and subjecting the cell to electrolysis conditions to remove the water from the coating formed by the solution, (3) dissolving the coating adjacent the inlet and outlet, and (4) removing the dissolved material.

Other aspects include a low level water measurement system combining the electrolytic cell having the characteristics described above and an associated electrical circuit for supplying power and measuring response to electrolysis, and methods of fabricating the cell and preparing (sensitizing) the cell for electrolysis.

DESCRIPTION OF THE DRAWINGS

The foregoing and other aspects, features and advantages of the invention will be apparent from the following description including the drawings, wherein.

DETAILED DESCRIPTION

Figure 1:
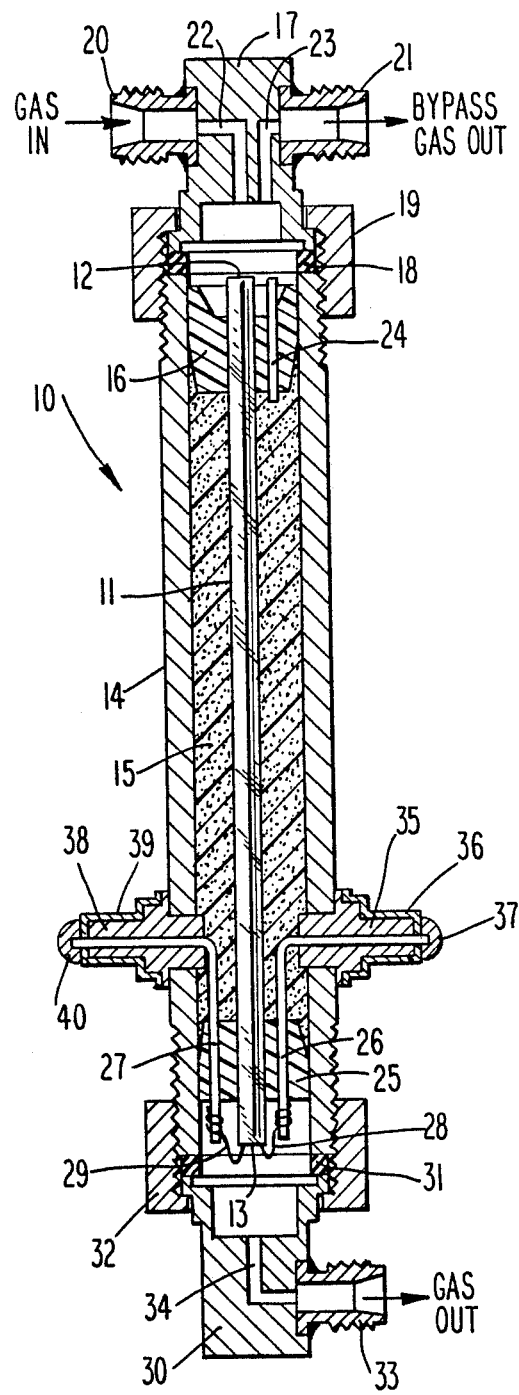
FIG. 1 is a longitudinal cross-sectional view of an electrolytic cell of the invention.

With reference to the drawings, FIG. 1 shows one embodiment of an electrolytic cell of the invention. The cell 10 includes a tubular electrode element 11 of glass, metal, plastic (such as polytetrafluoroethylene) or other suitable electrolytically inert material, glass being preferred. Element 11 defines a tubular conduit for passage of a gas and has an inlet 12 and an outlet 13, here shown at the extremities of the element but also locatable elsewhere in element 11. The element 11 is positioned concentrically in a protective housing or casing 14 conveniently formed of stainless steel but other materials including glass and plastic are suitable. A packing material 15, such as an epoxy potting compound, fills the concentric area between element 11 and the interior wall of housing 14. An inlet plug 16 formed of a resilient inert material such as polytetrafluoroethylene surrounds and concentrically positions the electrode element 11 at the upper (inlet) end of the cell. An inlet cap 17 is mounted in sealing engagement with a gasket 18 on the upper end of the housing 14, and is fixed in position thereon by a nut 19. Arms 20 and 21 mounted transversely of cap 17 operate as fittings for attachment of gas inlet and gas outlet (bypass) lines, respectively, either by threading engagement or by quick-coupling (not shown). Channel 22 conveys gas from fitting 20 through the interior of cap 17 to the inlet 12 of element 11. Channel 23 is a bypass conduit connecting the interior of cap 17 to fitting 21 for optional passage of gas from a source connected to fitting 20 to a collector connected to fitting 21. Extending through plug 16 is a tube 24 for admission of epoxy of other potting material during fabrication of the cell, as further explained below. Tube 24 is plugged by the potting material upon setting of the material.

The lower (outlet) end of element 11 is concentrically positioned in housing 14 by plug 25, conveniently formed of polytetrafluoroethylene. Received in plug 25 are leads 26 and 27 connected to the free ends 28 and 29 of wires 41 and 42 helically covering the interior of element 11 in a manner more fully described below with respect to FIGS. 2 and 3. A bottom cap 30 seats on a gasket 31 and is sealingly mounted on and engaged with housing 14 by nut 32. A gas outlet fitting 33 is conveniently mounted in cap 30 as a side arm and receives gas from the interiors of cap 30 and element 11 via a channel 34. Lead 26 extends externally of housing 14 through an electrically insulating packing 35 within a metallic contact arm 36 having a soldered tip 37. Similarly, lead 27 is received in an electrically insulating packing 38 in a metallic contact arm 39 mounted in housing 14 and having a soldered tip 40. Suitable packing materials are any electrically insulating substances such as polytetrafluoroethylene.

The electrode element 11, housing 14 and other structural elements of cell 10 may be dimensioned as convenient to suit flow rates of a gas for determination of water therein. In one configuration, tubular electrode element 11 is a five inch glass tubing having a ⅜ inch outside diameter and the housing 14 is ¾ inch outside diameter stainless steel tubing, but various other dimensions and materials can be employed.

Figure 2:
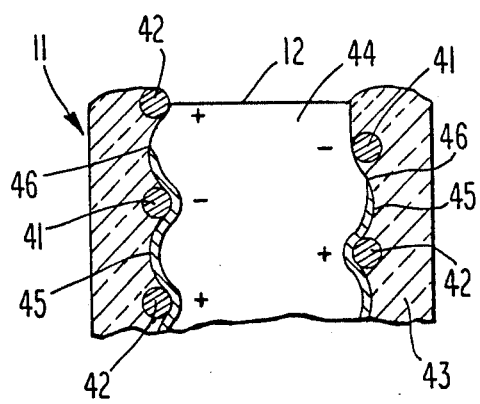
FIG. 2 shows details of the upper end of the electrode element of the cell of FIG. 1.
Figure 3:
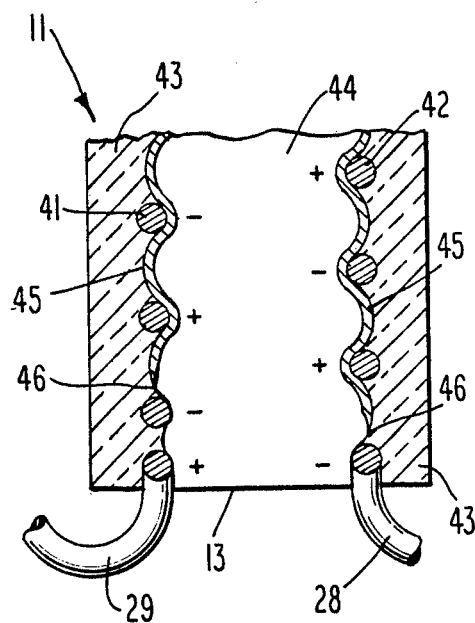
FIG. 3 shows details of the lower end of the electrode element of the cell of FIG. 1.

FIGS. 2 and 3 show details of the inlet (FIG. 2) and outlet (FIG. 3) portions (12,13) of tubular element 11. With respect thereto, wires 41 and 42 define electrodes of opposite polarity on the interior wall 43 of element 11. The wires 41 and 42 are positioned helically and in parallel, and the windings extend longitudinally of element 11 with suitable spacing between wires of opposite polarity for electrical isolation. The wires are shown partially embedded in the interior wall 43 of element 11. This results from the manufacturing technique explained below.

In a preferred embodiment of the invention, the wires 41 and 42 are wound substantially the full length of the interior cavity of element 11 exposed to gas passing from the inlet 12 to the outlet 13. Thus, as shown in FIGS. 2 and 3, wires 41 and 42 extend substantially to the inner edges of the inlet 12 and outlet 13 of element 11. Consequently, all water in the gas passing through element 11 will be subjected to electrolysis.

Wires 41 and 42 are coated with a water absorbent film 45 which is electrically conductive only upon absorption of water in the fluid passing through the element 11. Film 45 is preferably positioned such that it terminates at 46 just short of inlet 12 and outlet 13, whereby portions of the wires 41 and 42 adjacent the inlet and outlet are free of the absorbent film. This feature in combination with the alkylene oxide polymer present in the absorbent film and the positioning of the wires over substantially the entire face of the interior wall of element 11, including the wall portions adjacent the inlet and outlet, constitutes a preferred embodiment of the invention and facilitates achievement of the several advantages of the invention. Known electrolytic cells for water determination have been constructed substantially as shown in FIG. 1 but without the wire windings extending completely to the inlet and outlets of a tubular element, or without portions of wires adjacent the inlet and outlet being free of the absorbent film of the invention, preferably an alkylene oxide polymer. The result has been slow response time (of the order of 2 to 5 hours) as compared with response times of about one minute for cells of the present invention, and inability to achieve sensitivity over extended periods of time to low levels of water in a gas, of the order of about 2.000 to about 0.005 ppmv.

It is believed that a cause of the inefficiency of the known devices is that some water collects near the inlet and outlet, out of contact with electrodes, and therefore is not electrolyzed. Moreover, the presence of absorbent coating adjacent the inlet and outlet of prior devices is believed to remove water from the gas but without the water being electrolyzed. The portions of the prior cells adjacent the inlets and outlets therefore act as water reservoirs, preventing low level water determinations and even sometimes resulting in false readings.

Another characteristic of known electrolytic cells which also contributes to slow response times, poor sensitivity and poor longevity (lack of durability or stability) is the tendency of conventional phosphoric acid-derived absorbent crystalline coatings when repeatedly dried down to become embrittled and to develop discontinuities such as micro cracks. The discontinuities are believed to prevent transfer of moisture through the absorbent film to the wires for electrolysis.

To overcome these deficiences it was discovered that if the phosphoric acid solution, used to form the coating over the wires, is formulated with a water-soluble alkylene oxide polymer of a specific type and molecular weight, discontinuities in the crystalline phosphoric acid derivative film are prevented, despite numerous cycles of drying down and water determination. While prior electrolytic cells have employed organic hydroxy compounds with phosphoric acid in formulating water-absorbent coatings, the hydroxy compounds have been short chain diols, triols or carboxylic compounds, sometimes containing ether linkages intermediate in the chains. Representative of such compounds are glycerol, erythritol, tartaric acid, glycerol tricetate, polyvinyl acetate, hydrolyzed polyvinylacetate and methyl Carbitol. It is believed that the deficiencies of these additives result from the high proportion of hydroxyl and/or carboxyl groups to carbon such that the additives react with the phosphoric acid or derivative, thereby contributing to or at least not preventing formation of discontinuities in the absorbent film.

In accordance with a preferred embodiment of the present invention it has been found that several select classes of linear, water soluble, alkylene oxide polymers are effective in phosphoric acid-type water absorbent coatings to enhance water absorption and electrolysis, and to stabilize or reinforce the absorbent films, with the result that longevity and durability are greatly improved. Suitable alkylene oxide polymers are polyalkylene ($C_2$–$C_4$) glycols having average molecular weights of at least 500, and ethers or esters of polyalkylene ($C_2$–$C_4$) glycols, such ethers or esters having average molecular weights of at least 300. In the case of the glycol ethers and esters the average molecular weights may be lower than those of the glycols because etherification or esterification reduces the hydroxyl functionality available for reaction with the phosphoric acid or derivative. It is believed that such reaction decomposes the phosphoric acid or derivative, or otherwise reduces the absorbency thereof.

The molecular weight of the glycols, glycol ethers or glycol esters depends on the desired viscosity of the materials. Preferably, the glycols, ethers and esters should be freeflowing or viscous liquids at ambient temperatures. However, even waxy substances may be employed by heating the formulations, with suitable care being taken to avoid damaging the electrode element when flowing the composition into contact therewith. Generally, the molecular weights may range up to about 5000 or more. A preferred range is about 1000 to 3000 average molecular weight for all three classes of the alkylene oxide polymers.

Typical polyalkylene ($C_2$–$C_4$) oxides useful in the invention are polyethylene glycol, polypropylene glycol, polytetramethylene ether glycol, alkyl ($C_1$–$C_6$) ethers such as the monomethyl and monoethyl ethers of polyethylene glycol and the dimethyl and diethyl ethers of polyethylene glycol, and the various fatty esters of polyethylene glycol, such as the mono and diesters from stearic, lauric, oleic and tallow or tall oil fatty acids. The foregoing and other alkylene oxide polymers are commercially available from a variety of sources.

The phosphoric acid or phosphoric acid derivative component of the absorbent coating is any partially or fully hydrated $P_2O_5$, such as $HPO_3$, $H_3PO_4$ or any $P_2O_5$ based compound having water absorbent properties as described, for example, in the Smith & Mitchell text cited above, pages 569–660.

The glycols, glycol ethers or glycol esters may be used singly or in any mixture of two or more thereof, and in amounts which are effective to enhance the film forming properties of the phosphoric acid or phosphoric acid derivative formulation, and to reinforce the resulting film. The alkylene oxide polymer and phosphoric acid or derivative are formulated in aqueous solution usually with a volatile, polar organic solvent having a high dielectric constant, e.g., of about 10 to 60, such that any residue of solvent in the film will not undergo electrolysis. The solvent should also be inert to the phosphoric acid or derivative. Suitable solvents include acetone, acetonitrile, dioxane and diethyl ether.

The ratio of phosphoric acid or derivative to the alkylene oxide polymer in the formulation may range widely, a typical range being about 50:1 to about 5:1 by weight, more preferably about 30:1 to 10:1 by weight. The higher the molecular weight of the alkylene oxide polymer, the lower the amount required. The amount of water in the formulation should be sufficient to bring the alkylene oxide polymer into solution but should be as low as possible in order to reduce the amount of water which must be removed from the film by electrolysis before the cell can be used. A typical formulation may contain about 5 to 10 parts by volume of 85% phosphoric acid, about 1 to 10 parts by volume of water, about 0.1 to 1.0 parts by weight of the monomethyl ether of polyethylene glycol (1900 average molecular weight) and about 10 to 15 parts by volume of acetone. The formulation may also contain other additives, such as surfactants and spreading or coupling agents, to facilitate the coating of the electrode wires. Suitable additives are described in the Smith & Mitchell text cited above.

FABRICATION AND SENSITIZATION OF THE CELL

The electrode element 11 of the cell of the invention is fabricated in a generally conventional manner by winding pairs of platinum or other noble metal electrode wire on an iron mandrel, the noble metal wires being spaced apart by copper wire, inserting the mandrel in a tubular conduit, for example, of glass or polytetrafluorethylene, fusing the conduit material to the wires on the mandrel, and then stretching the mandrel so that it can be removed from the conduit, leaving the wires fused to the inner wall of the conduit. The copper wires are then dissolved with nitric acid, external leads are attached to ends of the wires, and the leads are mounted on contacts. The electrode element including external leads is then positioned, as shown in FIG. 1, in a housing 14, plugs 16 and 25 are inserted, the space between the housing and the electrode element is filled through a tube 24 with a suitable potting material 15 such as epoxy, and caps 17 and 30 with fittings and gas lines are placed on the ends of the device to complete the cell. Other details of fabrication are described in the Keidel article and Smith & Mitchell text cited above.

The electrode element is then sensitized by admitting a phosphoric acid solution to the element to coat the wires on the interior wall of the element. The coating is dried down to a hygroscopic state by passing dry nitrogen gas through the conduit, thereafter adding a few drops of acetone to the conduit to remove loose coating material, and electrolyzing.

To construct cells of the invention, however, several significant deviations from the foregoing procedure are required. The first change is taking care to insure that the electrode wires cover substantially the entire face of the interior wall of the electrode element 11 (FIGS. 1–3). This is achieved by winding the electrode and copper wires on the iron mandrel a distance greater than the length of the conduit and soldering the wires on the mandrel (top and bottom) before insertion into the conduit, so that the wires extend out of the conduit (top and bottom). The wires are then fused into the conduit wall from top to bottom and excess wire is cut against the mandrel from the top (inlet) end of the conduit. The mandrel is stretched and removed. The copper wire is then dissolved and the remaining steps of fabrication completed.

The second change is in the sensitization process. The electrode wires are coated with the phosphoric acid-/alkylene oxide polymer formulation and a dry inert gas in passed through the conduit of the electrode element followed by electrolysis in order to dry down the film to a hygroscopic state. However, after the dry down treatment, small portions of the film adjacent the inlet and outlet are removed. This is conveniently achieved by adding a few drops (e.g., 1-5 drops) of a solvent (such as acetone) for the film to one end of the conduit and removing the dissolved material by passing a dry inert gas (such as nitrogen) through the conduit, optionally thereafter electrolyzing the system. This same procedure is then applied to the other end of the conduit. In this manner, small portions (about 1-5 mm, preferably 2-3 mm) of the film are removed from the wires adjacent the inlet and outlet of the electrode element, thereby providing the improved characteristics described above.

Cleanliness of the gas inlet channels 22 and connecting channels and lines is important for efficient operation of the system. Channel 22 in particular must be free of adherent particles such as metal particles from fabrication. Various cleaning and polishing methods and materials are useful for this purpose, such as a commercial alumina polish which may be applied by means of a knotted string passed through the channels and lines. An inert gas is then passed through channel 22 while the cell is in a gas bypass mode, i.e., with outlet valving closed, such that the gas passes through the cap 17 and out via channel 23. By this means a finish can be obtained having an average irregularity of about one micron or less.

POWER SUPPLY

Figure 4:
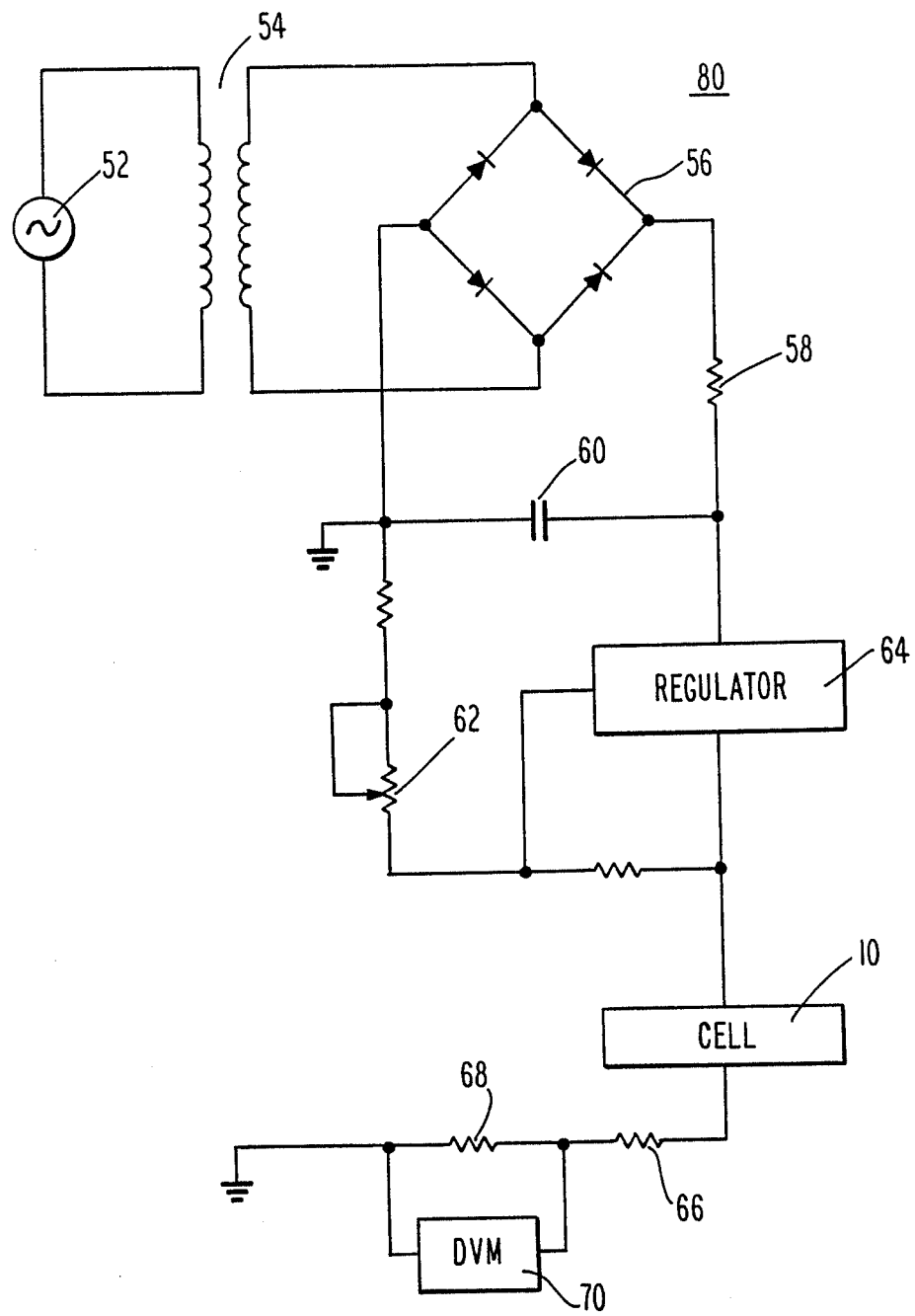
FIG. 4 is a schematic of the associated electrical circuits utilized with an electrolytic cell of the invention, such as that of FIG. 1.

Referring now to FIG. 4, there is shown a power supply for use with an electrolytic cell in a water measurement system of the present invention. Power supply 80 includes AC source 52 and transformer 54 for providing AC power to rectifier 56 in a conventional manner. Current limiting resistors 58,66 and damping capacitor 60 are also provided in a conventional manner. Transformer 54 and regulator 64 are selected to provide approximately seventy-five volts to cell 10. Potentiometer 62 is provided for trimming in a conventional manner.

Because the current through cell 10 is equal to the current through precision resistor 68, digital voltmeter 70 is provided to indirectly determine the current through cell 10 by measuring the voltage drop across precision resistor 68. The current through cell 10 which is indirectly measured by digital volt meter 70 is representative of the amount of moisture in a gas passed through cell 10.

Very low currents are produced in cell 10 in response to moisture in the below one part per million range. These currents are in the range of microamps because cell 10 has an extremely high resistance in this moisture range. For example, the resistance of cell 10 may be on the order of one hundred to two hundred megaohms in this moisture range. This causes voltage and current measurements, especially active voltage or current measurements, designed to determine the current through cell 10 to drift and to be unreliable in this low-moisture, high-resistance range of cell 10. Active devices, when placed in the series circuit position of, for example, resistor 68 tend to drift because they do not operate well in the microamp range.

To avoid this drift, a passive device resistor 68 is selected rather than an active one. Resistor 68 is selected to be a very low temperature coefficient, high precision device for providing passive rather than active measurement. The precision of resistor 68 may be further insured by selecting resistor 68 from a plurality of known precision resistors.

OPERATION OF THE SYSTEM

Figure 5:
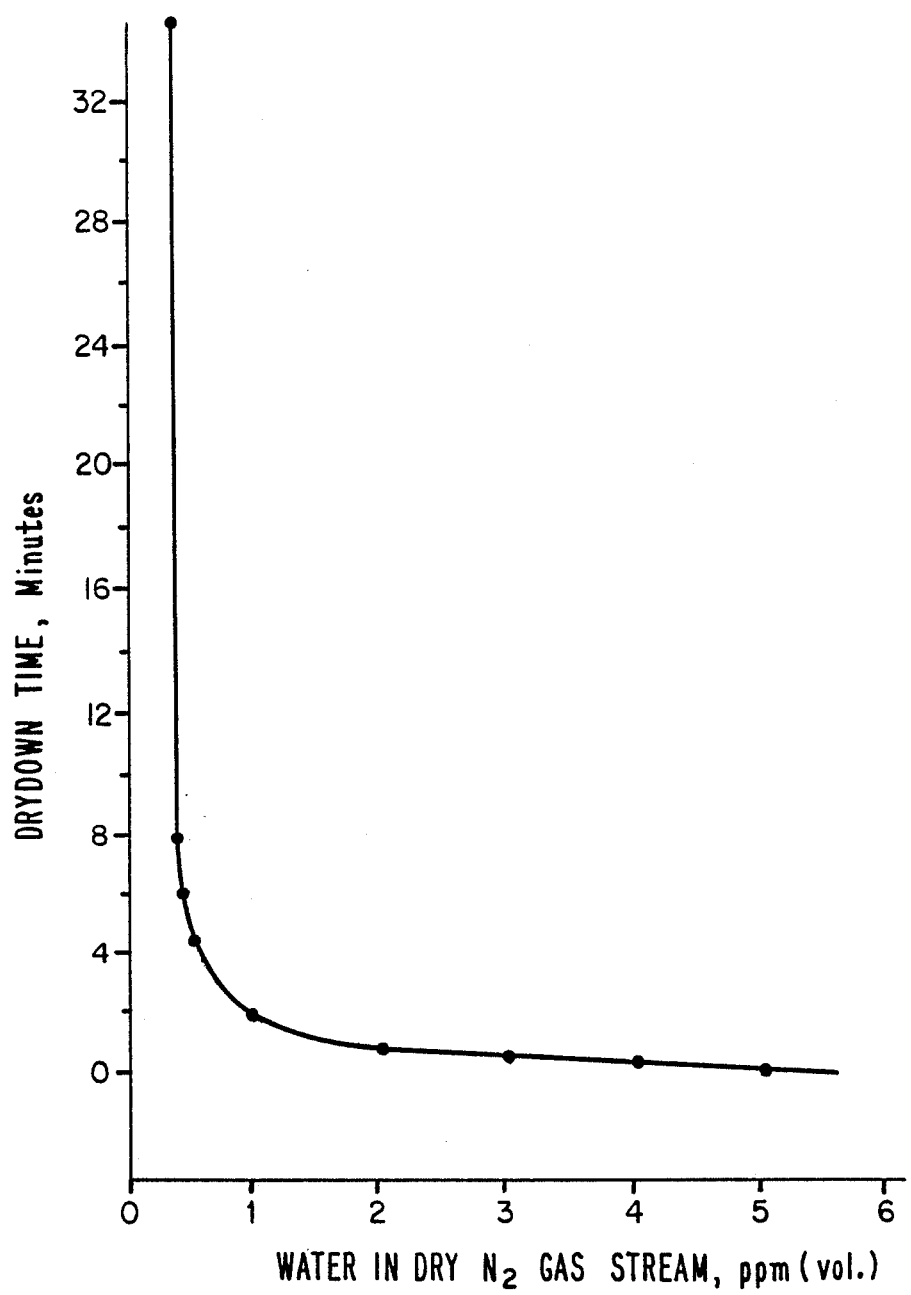
FIG. 5 is a graph illustrating response time of an electrolytic cell of the invention, such as that of FIG. 1, to achieve a base line dry state preparatory to measurement of water in a gas.

The system is generally operated in the manner described in U.S. Pat. No. 2,830,945 and in the publications cited above. However, its exceptional response time, longevity and sensitivity is demonstrated from the representative recorder trace (FIG. 5) of response time for equilibrating a cell 10 of the invention to a baseline dry state. In the test procedure, the cell was first equilibrated with a gas stream (such as nitrogen) carrying at least 5 ppmv water. Equilibration required about 20 minutes. The wet gas was then shut off and a dry gas such as nitrogen run through the cell simultaneously with recording of moisture removal. As shown in FIG. 5, at zero time about 5 ppmv of water was in the system. At 1 minute the water decreased to about 2 ppmv and at 2 minutes the water was down to 1 ppmv. At about 5 minutes the system had dried down to about 0.5 ppmv, and after 8 minutes there was essentially no change. The final data point was 0.17 ppmv. The response time remained consistent after more than six weeks, thus demonstrating the exceptional sensitivity, longevity and response time of the system.

Although the cell and water measurement system of the invention are effective for low level water measurement, it will be understood that the invention is also applicable to the measurement of higher water levels, up to about 2000 ppmv or higher.

It will also be understood that the foregoing embodiments of the invention are illustrative only, and that various changes can be made in the form, details, spatial arrangements, materials and proportions of the various parts in such embodiments without departing from the spirit and scope of the invention as defined by the appended claims.

We claim:

1. An electrolytic cell for low level measurement of water in a gas, comprising the combination of:
    a tubular conduit for a gas,
    a gas inlet and a gas outlet in the conduit,
    fittings on the inlet and outlet including channels therein for flow of the gas,
    at least one pair of electrically isolated wires helically disposed in parallel on the interior wall of the conduit,
    exterior leads connected to the wires,
    said wires covering substantially the entire face of the interior wall exposed to the gas between the inlet and outlet, and
    a water absorbent coating on the wires, said coating being electrically conductive only upon absorption of water in the gas, wherein portions of the wires adjacent the inlet and outlet, interior of the tubular conduit, are free of the absorbent coating.

2. A low level water measurement system comprising, in combination, the electrolytic cell of claim 1,
    a power supply coupled to one of the exterior leads for providing electrical power to the cell, a series resistor coupled to the other exterior lead for providing a current through the resistor equal to the current through the cell, and voltage measurement means coupled to the resistor for measuring the voltage across the resistor, thereby providing a measure of the current through the resistor.

3. A process for determining the amount of water in a gas, which comprises passing said gas through the cell of claim 1 for a time sufficient to absorb the water therein into the coating on the electrode wires of said cell, electrolyzing said water, and recording the amount of water as a function of the current required to effect said electrolysis.

4. An electrolytic cell for low level measurement of water in a gas, comprising the combination of:
a tubular conduit for a gas,
a gas inlet and a gas outlet in the conduit,
fittings on the inlet and outlet including channels therein for flow of the gas,
at least one pair of electrically isolated wires helically disposed in parallel on the interior wall of the conduit,
exterior leads connected to the wires, and
a water absorbent coating on the wires, said coating being electrically conductive only upon absorption of water in the gas and comprising a mixture of phosphoric acid or a derivative thereof and a film forming and reinforcing amount of a water soluble alkylene ($C_2 \propto C_4$) oxide polymer selected from a polyalkylene glycol, a polyalkylene glycol ether and a polyalkylene glycol ester, said glycol having an average molecular weight of at least 500 and said ether and ester having an average molecular weight of at least 300.

5. The electrolytic cell of claim 4 wherein the wires coated with the alkylene ($C_2$–$C_4$) polymer cover substantially the entire face of the interior wall between the inlet and outlet.

6. The cell of claim 5 wherein portions of the wires adjacent the inlet and outlet, interior of the tubular conduit, are free of the absorbent coating.

7. A low level water measurement system comprising, in combination, the electrolytic cell of claim 5,
a power supply coupled to one of the exterior leads for providing electrical power to the cell,
a series resistor coupled to the other exterior lead for providing a current through the resistor equal to the current through the cell, and
voltage measurement means coupled to the resistor for measuring the voltage across the resistor, thereby providing a measure of the current through the resistor.

8. A process for determining the amount of water in a gas, which comprises passing said gas through the cell of claim 5 for a time sufficient to absorb the water therein into the coating on the electrode wires of said cell, electrolyzing said water, and recording the amount of water as a function of the current required to effect said electrolysis.

9. The cell of claim 4 wherein the alkylene oxide polymer is a polyethylene glycol ether having an average molecular weight of about 300 to 5000.

10. The cell of claim 4 wherein the alkylene oxide polymer is a polyethylene glycol ester having an average molecular weight of about 300 to 5000.

11. The cell of claim 4 wherein the ratio of phosphoric acid or derivative to the alkylene oxide polymer in the coating is from about 50:1 to about 5:1 by weight.

12. The cell of claim 4 wherein the alkylene oxide polymer is a polyethylene glycol mono methyl ester having an average molecular weight of about 300 to 5000.

13. A low level water measurement system comprising, in combination, the electrolytic cell of claim 4,
a power supply coupled to one of the exterior leads for providing electrical power to the cell,
a series resistor coupled to the other exterior lead for providing a current through the resistor equal to the current through the cell, and
voltage measurement means coupled to the resistor for measuring the voltage across the resistor, thereby providing a measure of the current through the resistor.

14. A process for determining the amount of water in a gas, which comprises passing said gas through the cell of claim 4 for a time sufficient to absorb the water therein into the coating on the electrode wires of said cell, electrolyzing said water, and recording the amount of water as a function of the current required to effect said electrolysis.

15. A method of sensitizing an electrolytic cell for low level measurement of water in a gas, said cell including, in combination, a tubular conduit for the gas, a gas inlet and a gas outlet in the conduit, at least one pair of electrically isolated wires helically disposed in parallel on the interior wall of the conduit and covering substantially the entire face of the interior wall exposed to the gas between the inlet and outlet;
said method comprising (1) coating substantially the entire surface of the wires on the interior wall of the conduit with an aqueous solution of phosphoric acid or a phosphoric acid derivative and a film forming and reinforcing amount of a water soluble alkylene ($C_2$–$C_4$) oxide polymer selected from a polyalkylene glycol, a polyalkylene glycol ether and a polyalkylene glycol ester, said glycol having an average molecular weight of at least 500 and said ether and ester having an average molecular weight of at least 300, (2) passing a dry inert gas through the conduit and subjecting the cell to electrolysis conditions to remove the water from the coating formed by the solution, (3) dissolving the coating adjacent the inlet and outlet, and (4) removing the dissolved material.

16. The method of claim 15 wherein the coating is dissolved in step (3) by introducing a minor amount of a volatile organic solvent into one of the inlet and outlet, removing the dissolved material, and repeating said introduction and removal on the other of the inlet and outlet.

17. The method of claim 16 wherein the dissolved material is removed by passing a dry, inert gas through the conduit.

18. The method of claim 17 wherein, after passage of the gas, the cell is subjected to electrolysis conditions.

19. The method of claim 16 wherein the organic solvent is acetone and the minor amount is about 1–5 drops.

* * * * *